United States Patent
Peterson et al.

(10) Patent No.: US 11,878,133 B2
(45) Date of Patent: Jan. 23, 2024

(54) METHODS OF PREPARING BALLOON EXPANDABLE CATHETERS FOR CARDIAC AND VASCULAR INTERVENTIONS

(71) Applicant: MEDTRONIC, INC., Minneapolis, MN (US)

(72) Inventors: Justin Peterson, Santa Rosa, CA (US); Victoria Ung, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 731 days.

(21) Appl. No.: 16/940,465

(22) Filed: Jul. 28, 2020

(65) Prior Publication Data

US 2021/0100988 A1 Apr. 8, 2021

Related U.S. Application Data

(60) Provisional application No. 62/912,179, filed on Oct. 8, 2019.

(51) Int. Cl.
*A61M 25/10* (2013.01)

(52) U.S. Cl.
CPC . *A61M 25/10182* (2013.11); *A61M 2210/125* (2013.01)

(58) Field of Classification Search
CPC ...... A61M 25/10182; A61M 2210/125; A61M 25/104; A61M 2025/1077
See application file for complete search history.

(56) References Cited

U.S. PATENT DOCUMENTS

| | | |
|---|---|---|
| 1,942,353 A | 1/1934 | Kornel |
| 3,248,184 A | 4/1966 | Livesay et al. |
| 3,483,723 A | 12/1969 | Verkaik |
| 3,570,014 A | 3/1971 | Hancock |
| 3,845,903 A | 11/1974 | Runniger |
| 4,106,129 A | 8/1978 | Carpentier et al. |
| 4,532,793 A | 8/1985 | Bezold |
| 4,626,255 A | 12/1986 | Reichart |
| 4,685,321 A | 8/1987 | Van den Berg et al. |

(Continued)

FOREIGN PATENT DOCUMENTS

| | | | |
|---|---|---|---|
| AU | 2003200619 A1 | * 9/2004 | ......... A61B 18/1492 |
| KR | 100488673 B1 | * 5/2005 | |

OTHER PUBLICATIONS

English Translation of KR-100488673-B1 (Year: 2005).*
International Search Report and Written Opinion dated Jan. 19, 2021, in Intl. Appl. No. PCT/US2020/053725.

*Primary Examiner* — Nilay J Shah (74) *Attorney, Agent, or Firm* — MEDLER FERRO WOODHOUSE & MILLS PLLC (57) ABSTRACT

Methods for purging a balloon catheter of air. An inflation fluid is inserted into a balloon and an inflation lumen of a balloon catheter. The inflation lumen is in fluid communication with the balloon. The balloon catheter is positioned in an inverted orientation with a distal end thereof disposed below a proximal end thereof. The distal end of the balloon catheter includes a balloon. A vibration source is positioned in direct contact with an outer surface of the balloon catheter. The balloon catheter is vibrated via the vibration source. A vacuum is applied or pulled on the inflation lumen of the balloon catheter. The steps of vibrating the balloon catheter and applying the vacuum are performed simultaneously.

18 Claims, 5 Drawing Sheets

(56) References Cited

U.S. PATENT DOCUMENTS

| | | | |
|---|---|---|---|
| 4,793,351 A * | 12/1988 | Landman | A61M 25/10185 604/920 |
| 4,821,722 A | 4/1989 | Miller et al. | |
| 5,035,705 A * | 7/1991 | Burns | A61M 25/0075 604/99.02 |
| 5,334,153 A | 8/1994 | McIntyre et al. | |
| 5,489,298 A | 2/1996 | Love et al. | |
| 5,716,417 A | 2/1998 | Girard et al. | |
| 5,904,697 A | 5/1999 | Gifford, III | |
| 6,001,124 A | 12/1999 | Backinski | |
| 6,245,102 B1 | 6/2001 | Jayaraman | |
| 6,425,916 B1 | 7/2002 | Garrison | |
| 6,494,889 B1 | 12/2002 | Fleischman | |
| 6,733,525 B2 | 5/2004 | Yang et al. | |
| 7,100,416 B2 | 9/2006 | Suzumura | |
| 7,220,275 B2 | 5/2007 | Davidson et al. | |
| 7,267,680 B2 | 9/2007 | Wright | |
| 7,270,679 B2 | 9/2007 | Istephanous et al. | |
| 7,361,192 B2 | 4/2008 | Doty | |
| 7,374,571 B2 | 5/2008 | Pease et al. | |
| 7,419,597 B2 | 9/2008 | Brugger et al. | |
| 7,517,363 B2 | 4/2009 | Rogers et al. | |
| 7,871,436 B2 | 1/2011 | Ryan et al. | |
| 8,025,714 B2 | 9/2011 | Prisco et al. | |
| 8,500,801 B2 | 8/2013 | Eberhardt et al. | |
| 2002/0143294 A1 | 10/2002 | Duchon et al. | |
| 2003/0014104 A1 | 1/2003 | Cribier | |
| 2003/0130726 A1 | 7/2003 | Thorpe et al. | |
| 2003/0208261 A1 | 11/2003 | Thorpe et al. | |
| 2004/0138737 A1 | 7/2004 | Davidson et al. | |
| 2005/0033343 A1 * | 2/2005 | Chermoni | A61M 25/0122 606/191 |
| 2005/0267581 A1 | 12/2005 | Marnay et al. | |
| 2006/0020341 A1 | 1/2006 | Schneid et al. | |
| 2006/0173537 A1 | 8/2006 | Yang et al. | |
| 2006/0271161 A1 | 11/2006 | Meyer | |
| 2008/0109081 A1 | 5/2008 | Bao et al. | |
| 2008/0215144 A1 | 9/2008 | Ryan | |
| 2008/0249619 A1 | 10/2008 | Stacchino et al. | |
| 2008/0255660 A1 | 10/2008 | Guyenot et al. | |
| 2009/0005863 A1 | 1/2009 | Goetz | |
| 2009/0062920 A1 | 3/2009 | Tauber | |
| 2009/0082867 A1 | 3/2009 | Sebastian et al. | |
| 2009/0132052 A1 | 5/2009 | Baccelli et al. | |
| 2009/0223952 A1 | 9/2009 | Wnek | |
| 2009/0248139 A1 | 10/2009 | Pellegrini | |
| 2010/0049306 A1 | 2/2010 | House et al. | |
| 2010/0049313 A1 | 2/2010 | Alon et al. | |
| 2010/0256723 A1 | 10/2010 | Murray | |
| 2011/0040374 A1 | 2/2011 | Goetz et al. | |
| 2013/0053693 A1 | 2/2013 | Breznock et al. | |
| 2015/0343191 A1 * | 12/2015 | Spano | A61M 25/10 604/22 |

* cited by examiner

METHODS OF PREPARING BALLOON EXPANDABLE CATHETERS FOR CARDIAC AND VASCULAR INTERVENTIONS

CROSS-REFERENCE TO RELATED APPLICATIONS

This application claims the benefit of U.S. Provisional Patent Application No. 62/912,179 filed Oct. 8, 2019.

FIELD OF THE INVENTION

The present disclosure relates to balloon catheters, and more particularly to methods of purging air from balloon catheters prior to use in an interventional procedure.

BACKGROUND OF THE INVENTION

Balloon catheters are conventionally used in a wide variety of medical procedures. For example, a balloon is inflated during percutaneous transluminal coronary angioplasty (PTCA) to dilate a stenotic blood vessel and may also be used to deliver a stent to support the vessel lumen in an open position. Typically, balloon inflation is accomplished by injecting an inflation fluid under pressure into an inflation lumen of a balloon catheter. As the pressure of the inflation fluid within the balloon catheter increases during use, there is a possibility that the balloon may burst due to excess pressure of the inflation fluid. If such bursting occurs, the inflation fluid inside the catheter will enter the blood stream of the patient. Normally, the pressurizing inflation fluid is a saline or other physiologically inert solution which should not cause harm to the patient. However, should there be any air within the catheter, bursting of the balloon might release air into the patient's blood vessel with the possibility that an air embolus might be formed. Therefore, balloon catheters must be purged of air prior to use to eliminate the risk of an air embolism entering a vessel if the system were to leak or the balloon were to rupture. The air also must be evacuated from the balloon to accomplish a desired inflation of the balloon using a specific volume of inflation fluid without the need to account for compression of an unknown volume of air within the balloon.

Since the balloon is used in arteries and veins, an inflation media must be selected which will avoid serious injury to the patient should the media be accidentally released into the body. Radiopaque contrast media, either 100% or in solution with water or saline, is typically employed to fill and purge the balloon of all harmful gases. As described above, air removal is essential not only to ensure the safety of the patient but also to prevent air blocks which could limit the amount of expansion of the balloon, thereby reducing the effectiveness of the procedure.

A common method of purging air from a balloon catheter prior to use involves creating a vacuum inside the inflation lumen of the balloon catheter, typically in conjunction with a syringe used for inflation fluid filling purposes. Inflation fluid is injected into the inflation lumen and air is drawn into the syringe. In such a procedure, air which has been purged from the catheter collects in the syringe, which is removed from the catheter so that air in the syringe may be expelled. These steps may have to be repeated multiple times to adequately purge the catheter of air, requiring a substantial amount of labor and preparation time. Depending on the size of the balloon, and therefore the volume of fluid and bubbles in the balloon catheter, the preparation time can reach up to thirty minutes. Long preparation time is particularly an issue for the larger balloon catheters such as those used to implant a replacement heart valve.

Accordingly, it would be desirable to provide a method of purging air from balloon catheters that requires less preparation time.

SUMMARY OF THE INVENTION

Embodiments hereof relate to a method for purging a balloon catheter of air. In an embodiment, an inflation fluid is inserted into a balloon and an inflation lumen of a balloon catheter. The inflation lumen is in fluid communication with the balloon. The balloon catheter is positioned in an inverted orientation with a distal end thereof disposed below a proximal end thereof. The distal end of the balloon catheter includes a balloon. A vibration source is positioned in direct contact with an outer surface of the balloon catheter. The balloon catheter is vibrated via the vibration source to cause air within the balloon of the balloon catheter or air within the inflation lumen of the balloon catheter to move upwards towards the proximal end of the balloon catheter.

In another embodiment, an inflation fluid is inserted into a balloon and an inflation lumen of a balloon catheter. The inflation lumen is in fluid communication with the balloon. The balloon catheter is positioned in an inverted orientation with a distal end thereof disposed below a proximal end thereof. The distal end of the balloon catheter includes a balloon. A vibration source is positioned in direct contact with an outer surface of the balloon catheter. An inflation fluid is inserted into the balloon and the inflation lumen of the balloon catheter. A vacuum is applied or pulled on the inflation lumen of the balloon catheter. The balloon catheter is vibrated via the vibration source while applying the vacuum on the inflation lumen of the balloon catheter to cause air within the balloon of the balloon catheter or air within the inflation lumen of the balloon catheter to move upwards through the inflation fluid towards the proximal end of the balloon catheter.

In another embodiment, an inflation fluid is inserted into a balloon and an inflation lumen of a balloon catheter. The inflation lumen is in fluid communication with the balloon. The balloon catheter is positioned in an inverted orientation with a distal end thereof disposed below a proximal end thereof. The distal end of the balloon catheter includes a balloon. A vibration source is positioned in direct contact with an outer surface of the balloon catheter. The balloon catheter is vibrated via the vibration source. A vacuum is applied or pulled on the inflation lumen of the balloon catheter. The steps of vibrating the balloon catheter and applying the vacuum are performed simultaneously.

BRIEF DESCRIPTION OF THE DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" is a position distant from or in a direction away from the clinician. "Proximal" or "proximally" is a position near or in a direction toward the clinician.

The following detailed description is merely exemplary in nature and is not intended to limit the invention or the application and uses of the invention. Although the description of the invention is in the context of balloon catheters utilized in treatment of a heart valve, the invention may also be used where it is deemed useful in other valved intraluminal sites that are not in the heart or in the context of treatment of blood vessel or other body passageways. Further, the invention has applicability to all balloon expandable devices and any balloon catheter that may be purged of air prior to use thereof. Stated another way, the invention has broad applicability across all vascular interventions that involve a balloon catheter. Furthermore, there is no intention to be bound by any expressed or implied theory presented in the preceding technical field, background, brief summary or the following detailed description.

Embodiments hereof relate to a method of purging a balloon catheter of air prior to an interventional procedure. More particularly, embodiments hereof relate to the application of a vibration source to expeditiously remove bubbles, or voids, from a balloon catheter prior to use. Methods described herein substantially reduce the length of the catheter preparation time by applying a vibration source to expedite bubble removal from the balloon catheter. To facilitate the air removal process, a vibration source is placed in direct contact with certain external parts of the catheter. This vibratory action causes the entrapped bubbles to rise through the column of inflation fluid and exit the catheter. This vibratory action significantly reduces the catheter preparation time. For example, in an embodiment, the catheter preparation time may be reduced from approximately 15-30 minutes when air is purged from a relatively large balloon catheter using conventional purging methods to less than 2 minutes for the same relatively large balloon catheter using vibratory action to expeditiously remove air as described in embodiments hereof. The shortened catheter preparation time reduces physical strain on staff, and also reduces overall procedure time which thereby increases potential patient volume and revenue for the catheter lab center.

Figure 1:
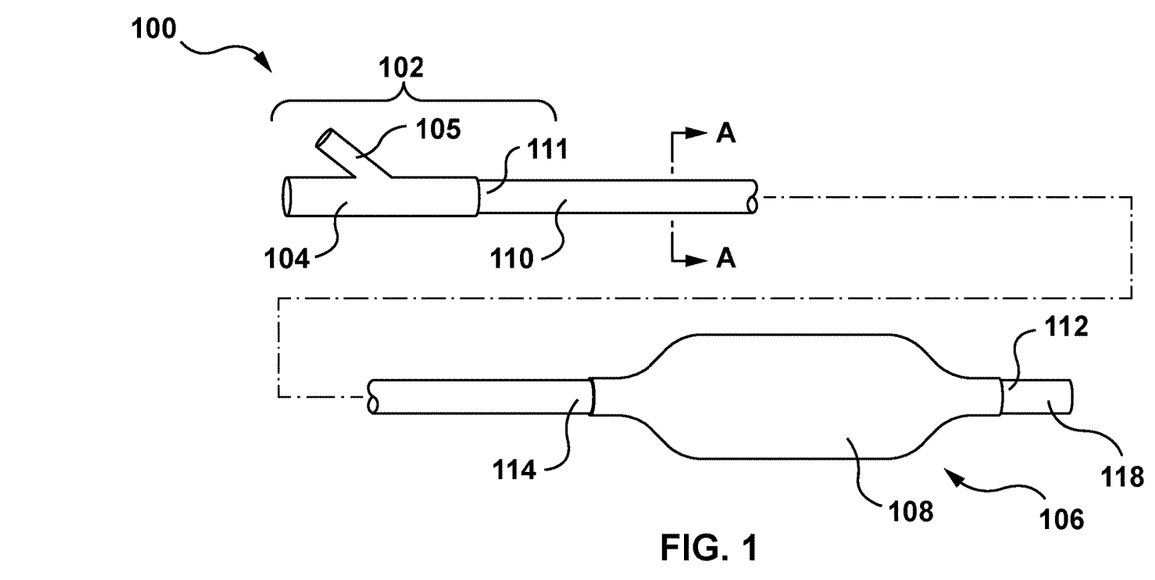
FIG. 1 is a side view of a balloon catheter in accordance with an embodiment hereof, wherein a balloon of the balloon catheter is in an expanded configuration.
Figure 1A:
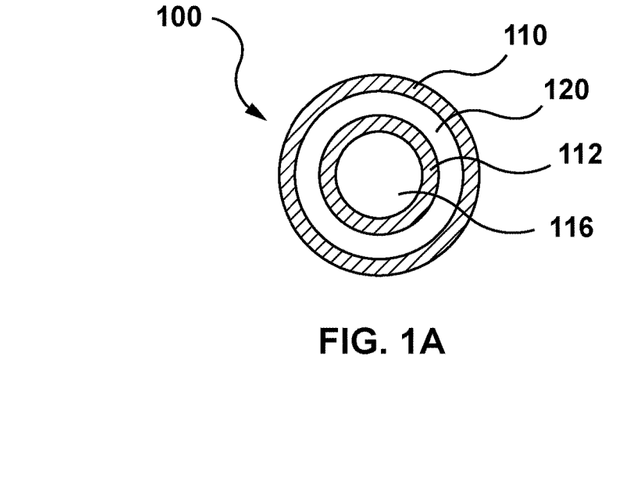
FIG. 1A is a cross-sectional view taken along line A-A of FIG. 1.

Turning now to the figures, FIGS. 1 and 1A depict an exemplary balloon catheter 100 that may be purged of air prior to use in an interventional procedure according to an embodiment hereof. In embodiments hereof, the balloon catheter 100 may form the basis of a prosthetic heart valve delivery system, a stent delivery system, a graft delivery system, and/or a drug delivery system. Stated another way, the balloon catheter 100 may be used to deliver a balloon-expandable device (not shown), such as a replacement heart valve, a stent, a graft, a drug delivery device, or another balloon-expandable device. Alternatively, the balloon catheter 100 may be utilized in a balloon angioplasty procedure. The objective in angioplasty is to restore adequate blood flow through the affected artery, which may be accomplished by inflating a balloon of a balloon catheter within the narrowed lumen of the artery to dilate the vessel.

The balloon catheter 100 includes a proximal portion 102 that extends out of the patient during clinical use and has a hub 104. As would be understood by one of ordinary skill in the art of balloon catheter design, the hub 104 includes a luer fitting 105 or other type of fitting that may be connected to a source of inflation fluid and may be of another construction or configuration without departing from the scope of the present invention. A distal portion 106 of the balloon catheter 100 is positionable at a target treatment location and includes an inflatable balloon 108, which is shown in an expanded or inflated configuration in FIG. 1. The balloon 108 may be made of a biocompatible material such as a thermoplastic polyurethane (TPU) resin, styrene-ethylene-butadiene-styrene (SEBS), PEBAX®, or the like.

With reference to the FIG. 1A which is a cross-sectional view taken along line A-A of FIG. 1, the balloon catheter 100 may have an over-the-wire (OTW) coaxial catheter configuration with an outer tubular component or shaft 110 and an inner tubular component or shaft 112. The outer shaft 110 has a proximal end 111 coupled to the hub 104 and a distal end 114 coupled to a proximal end of the balloon 108. The inner shaft 112 defines a guidewire lumen 116 extending substantially the entire length of the catheter for accommodating a guidewire (not shown). The inner shaft 112 has a proximal end (obscured from view in FIG. 1) coupled to the hub 104 and a distal end 118 terminating distally of the balloon 108 and defining a distal guidewire port. The inner shaft 112 extends coaxially within the outer shaft 110 such that an annular inflation lumen 120 is defined between an inner surface of the outer shaft 110 and an outer surface of the inner shaft 112. The inflation lumen 120 thus extends within the outer shaft 110 and into the inner volume of the balloon 108 to allow inflation fluid received through an inflation port of the luer fitting 105 of the hub 104 to be delivered to the balloon 108. A distal end of the balloon 108 is coupled to the inner shaft 112 distal of a distal end 114 of the outer shaft 110.

Figure 1B:
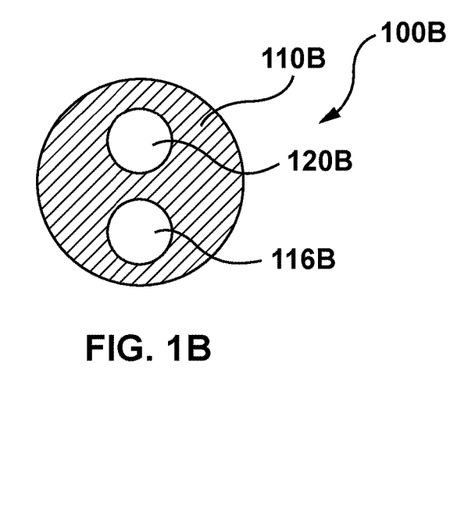
FIG. 1B is a cross-sectional view of a balloon catheter according to an alternate embodiment hereof.

Other types of catheter construction are also amendable to the invention, such as, without limitation thereto, a catheter shaft formed by multi-lumen profile extrusion. For example, an alternate catheter construction is illustrated in FIG. 1B, which is a cross-sectional view of a balloon catheter 100B according to an alternative embodiment. Rather than including coaxial inner and outer catheter shafts, the balloon catheter 100B includes a single catheter shaft 110B that defines an inflation lumen 120B and a guidewire lumen 116B, each extending substantially the entire length of the catheter and parallel to each other. Although depicted as circular in cross-section, one or more lumen(s) of the catheter shaft 110B may have any suitable cross-section including for example circular, elliptical, or crescent shapes.

In addition, the balloon catheter 100B may have a rapid-exchange configuration with the guidewire lumen extending only along a distal portion of the catheter, as understood by those of ordinary skill in the art.

Regardless of the type of catheter construction, the catheter shaft(s) may be formed of a polymeric material, non-exhaustive examples of which include polyethylene, polyethylene block amide (PEBA), polyamide and/or combinations thereof. Optionally, the catheter shaft(s) or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of the outer shaft 110 or catheter shaft 110B may be formed from a reinforced polymeric tube.

Figure 2:
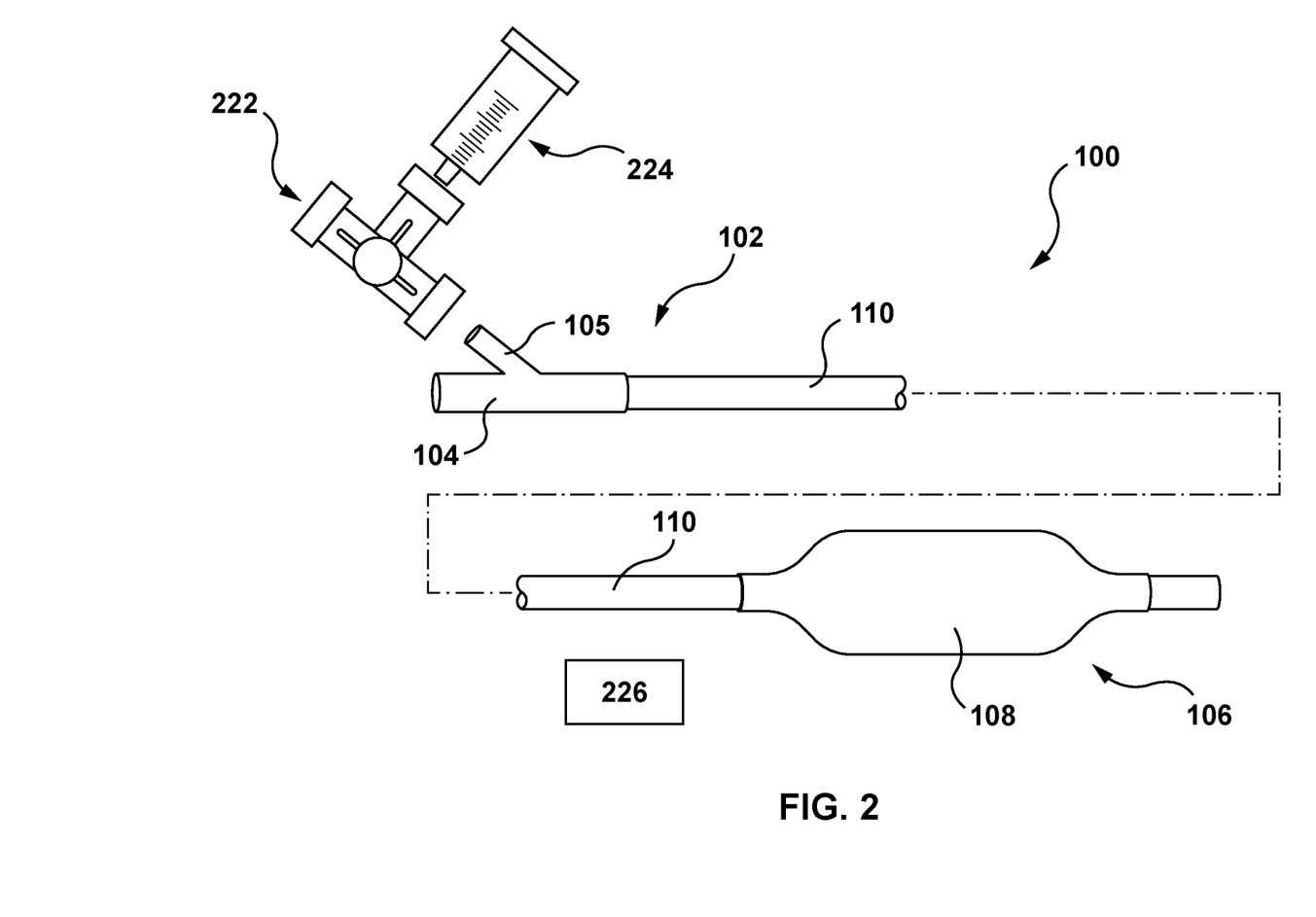
FIG. 2 is a side view of the balloon catheter of FIG. 1 and a stopcock, an inflator, and a vibration source, wherein the stopcock, the inflator, and the vibration source are accessories utilized in a method of purging air from the balloon catheter according to an embodiment hereof.

Turning now to FIG. 2, the balloon catheter 100 is shown in conjunction with a stopcock 222, an inflator 224, and a vibration source 226. The stopcock 222, the inflator 224, and the vibration source 226 are accessories or tools that are utilized in a method of purging air from the balloon catheter 100 prior to use in an interventional procedure according embodiments hereof. The stopcock 222 may be a three-way stopcock, and is configured to regulate the flow of an inflation fluid or gas therethrough, as known by persons having ordinary skill in the art. More particularly, as will be described in more detail herein, the stopcock 222 seals the balloon catheter 100 during application of a vacuum via the inflator 224 during the air purging methods described herein. The inflator 224 is configured to apply or pull a vacuum on the inflation lumen 120 of the balloon catheter 100 in order to purge air from the balloon 108 and the inflation lumen 120. In the embodiment depicted in FIG. 2, the inflator 224 is a syringe. Further, in addition to pulling a vacuum, the inflator 224 is also configured to hold an inflation fluid therein in order to flush the inflation lumen 120. The vibration source 226 is a tool that is configured to directly contact one or more external areas of the balloon catheter 100 to cause air entrapped in the balloon catheter 100 to exit from the balloon catheter 100, as will be described in more detail herein. For example purposes only, in an embodiment, the vibration source 226 may be a commercially available vortex mixer such as Vortex-Genie 2 available from Scientific Industries, Inc. of Bohemia, New York. In further embodiments, the vibration source 226 is a handheld tool that is configured to be held by a user and is configured to make direct physical contact with the outer surface of the balloon 108 and/or the outer surface of the outer shaft 110 or the shaft 110B.

Figure 3:
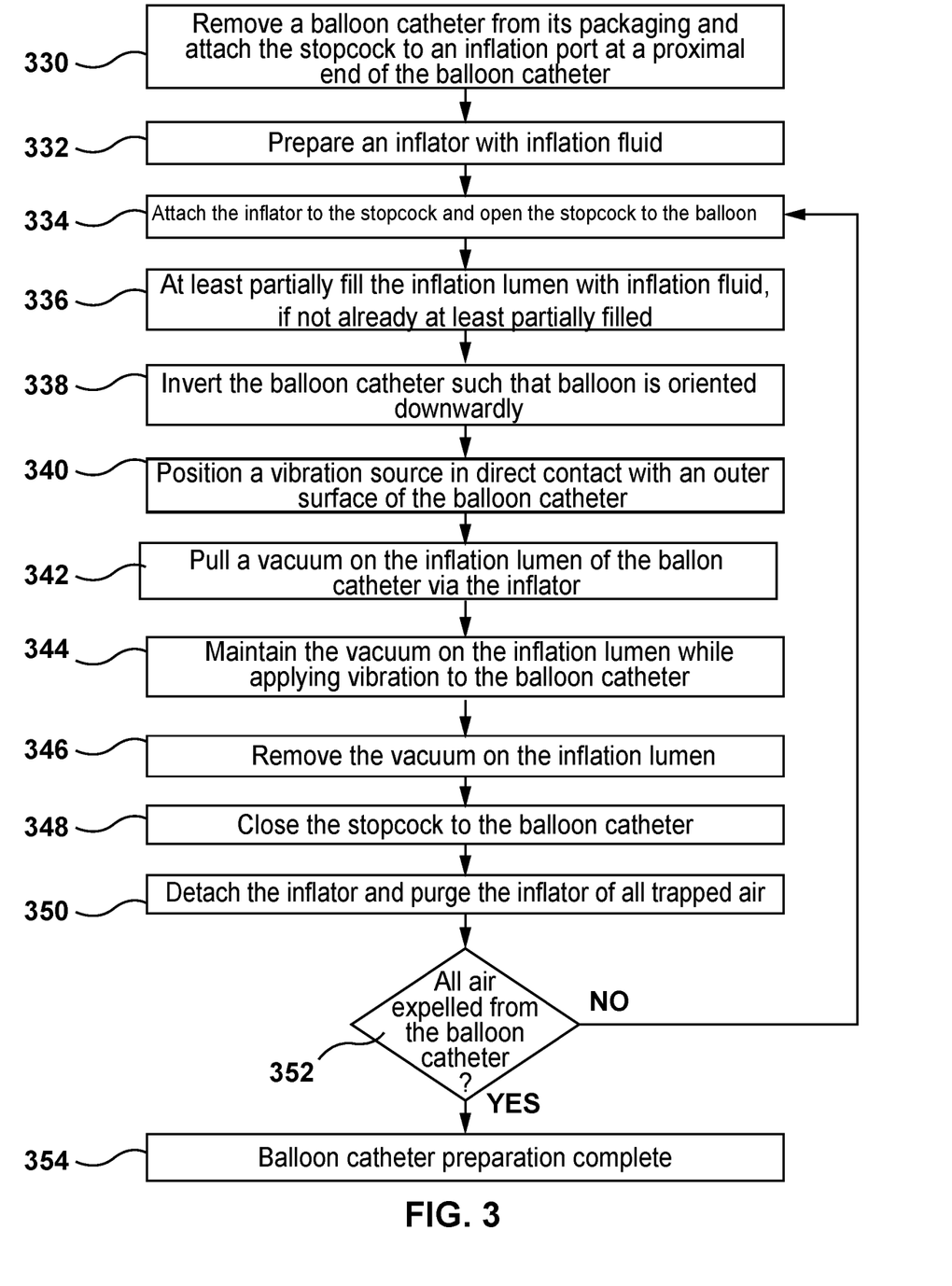
FIG. 3 is a flow chart illustrating a method of purging air from a balloon catheter according to an embodiment hereof.

Turning now to FIG. 3, a method for purging the balloon catheter 100 of air according to an embodiment hereof is shown. The method of FIG. 3 is preferably performed prior to an interventional procedure which utilizes the balloon catheter 100 in situ. This method is particularly advantageous for balloon catheters having larger balloons, such as but not limited to a balloon catheter configured as a delivery device for a replacement heart valve, because the method substantially reduces the length of the catheter preparation time by applying the vibration source 226 to expedite bubble/air removal from the balloon catheter as described above.

In a step 330, the balloon catheter 100 is removed from its packaging. The stopcock 222 is attached to the inflation port at the proximal portion 102 of the balloon catheter 100. More particularly, the stopcock 222 is attached to the inflation port of the luer fitting 105 of the hub 104 of the balloon catheter 100. As described above, the distal portion 106 of the balloon catheter 100 includes the balloon 108 and the inflation lumen 120 of the balloon catheter 100 is in fluid communication with the interior of the balloon 108. Although the method of FIG. 3 is described with respect to the balloon catheter 100, it will be understood by those of ordinary skill in the art that this is for sake of illustration only and the methods described herein for purging a balloon catheter of air may be utilized on balloon catheters of any construction and size.

In a step 332, the inflator 224 is prepared by at least partially filling the inflator 224 with an inflation fluid. In an embodiment, the inflator 224 is a syringe and the inflation fluid is a radiopaque contrast fluid, or a radiopaque contrast fluid mixed with saline or water. Other suitable biocompatible inflation fluids may be utilized.

In a step 334, the inflator 224 is attached to the stopcock 222 which was previously attached to the inflation port of the luer fitting 105 of the hub 104 of the balloon catheter 100 as described above and the stopcock 222 is opened to the balloon catheter 100. When the stopcock 222 is opened to the balloon catheter 100, the inflator 224 and the inflation lumen 120 of the balloon catheter 100 are in fluid communication and the inflation lumen 120 of the balloon catheter 100 is sealed with respect to atmosphere. Alternatively, the inflator 224 may be attached to the stopcock 222 and then the assembly of the inflator 224 and the stopcock 222 may be simultaneously attached to the inflation port at the proximal portion 102 of the balloon catheter 100.

In a step 336, the inflation lumen 120 is at least partially filled with the inflation fluid from the inflator 224. In order to at least partially fill the inflation lumen 120 with the inflation fluid from the inflator, the inflation fluid may be injected or inserted into the balloon 108 and the inflation lumen 120 of the balloon catheter 100 via the inflator 224 by advancing the plunger of the inflator 224. In another embodiment, in order to at least partially fill the inflation lumen 120 with the inflation fluid from the inflator, a vacuum may be applied or pulled on the inflation lumen 120 of the balloon catheter 100 via the inflator 224 and then the vacuum may be removed by slowly releasing the plunger of the inflator 224 to a neutral position, thereby at least partially filling the inflation lumen 120 with the inflation fluid from the inflator. More particularly, a user can manually apply or pull a vacuum on the inflation lumen 120 of the balloon catheter 100 by "pulling negative" or retracting the plunger of the inflator 224. When the plunger of the inflator 224 is released to a neutral position, the inflation fluid within the inflator 224 is drawn into the balloon catheter 100 and the inflation lumen 120 at least partially fills with the inflation fluid. Stated another way, removing the vacuum results in inflation fluid from the inflator 224 being pulled into the balloon catheter 100 such that the inflation lumen 120 and the balloon 108 are filled with the inflation fluid. The inflation fluid is drawn into the inflation lumen 120 and balloon 108 as a result of the pressure changes of the enclosed system.

In a step 338, the balloon catheter 100 is inverted or positioned in an inverted orientation such that the distal portion 106 including the balloon 108 is oriented below or downwardly relative to the proximal portion 102 of the balloon catheter and the inflator 224 coupled thereto. In an embodiment, the balloon catheter 100 is positioned in a vertical orientation with its distal end including the balloon 108 disposed vertically below the hub 104 and the inflator 224. However, the balloon catheter 100 is not required to be oriented vertically; the balloon catheter 100 may be oriented at an angle so long as the distal portion 106 thereof including the balloon 108 is oriented below or downwardly relative to the inflator 224. As will be described in more detail herein, the positioning of the inflator 224 above the balloon catheter 100 allows air bubbles to ascend or rise through the column of inflation fluid in the inflation lumen 120 and exit from the balloon catheter 100 via the inflator 224.

In a step 340, the vibration source 226 is positioned in direct contact with an outer surface of the balloon catheter. In an embodiment, the vibration source 226 is a handheld tool that is configured to be held by a user. In an embodiment, the vibration source 226 includes an outer surface configured to be held by a user and includes an inner surface (not shown) that is configured to make direct physical contact with the outer surface of the balloon 108 and/or the outer surface of the outer shaft 110. For example, the inner surface of the vibration source 226 may have a shape corresponding to the outer surface of the balloon 108 and/or the outer surface of the outer shaft 110.

In a step 342, a vacuum is applied or pulled on the inflation lumen 120 of the balloon catheter 100 via the inflator 224. More particularly, a user can manually apply or pull a vacuum on the inflation lumen 120 of the balloon catheter 100 by "pulling negative" or retracting the plunger of the inflator 224. Application of a vacuum results in the evacuation of air from the inflation lumen 120 of the balloon catheter 100. Stated another way, any residual air or gas is purged from the inflation lumen 120 of the balloon catheter 100 and the pressure within the inflation lumen 120 of the balloon catheter 100 is lowered to a pressure lower than atmospheric pressure. In an embodiment, any residual air or gas is purged from the inflation lumen 120 of the balloon catheter 100 until the pressure in the inflation lumen 120 is between 1 PSIA and 12 PSIA. During the step 342, the stopcock remains in its previous position ("open to the balloon catheter 100") and thereby seals the balloon catheter 100 while the inflator 224 pulls a vacuum on the inflation lumen 120 of the balloon catheter 100.

In a step 344, the vacuum is maintained on the inflation lumen 120 of the balloon catheter 100 via the inflator 224 while simultaneously applying vibration to the balloon catheter 100 via the vibration source 226. The balloon catheter 100 is vibrated via the vibration source 226 while applying the vacuum on the inflation lumen 120 of the balloon catheter 100 to cause air within the balloon 108 of the balloon catheter 100 or air within the inflation lumen 120 of the balloon catheter 100 to move upwards towards the proximal end of the balloon catheter 100 and the inflator 224. Stated another way, vibrating the balloon catheter 100 with the vibration source 226 causes any air or bubbles entrapped in the balloon catheter 100 to ascend out of the balloon 108 and inflation lumen 120 until such air or bubbles exit from the balloon catheter 100 and enter into the inflator 224. As air or bubbles exit from the balloon catheter 100 and enter into the inflator 224, the user can visually see such air or bubbles in the inflator 224. The vacuum is maintained on the inflation lumen 120 of the balloon catheter 100 via the inflator 224 while simultaneously applying vibration to the balloon catheter 100 until no new air or bubbles are seen entering into the inflator 224. For example, in an embodiment, the vacuum is maintained on the inflation lumen and vibration is simultaneously applied on the balloon catheter for between 15 and 45 seconds. In an embodiment, the vacuum is maintained on the inflation lumen and vibration is simultaneously applied on the balloon catheter for approximately 30 seconds. Although described herein that vibration is applied during the step 344, vibration may also be applied during previous method steps as well. For example, vibration may begin immediately after the vibration source 226 is placed into direct contact with the balloon catheter 100 or the vibration may begin prior to or at the same time as the step 342 when the vacuum is initially pulled or applied to the inflation lumen 120.

In an embodiment, during the step 344, the vibration source 226 is moved or slid along the outer surface of the balloon catheter 100 while vibrating the balloon catheter. For example, the vibration source 226 may originally be placed in direct physical contact with the outer surface of the balloon 108. As the air or bubbles entrapped in the balloon 108 ascend through the inflation lumen 120, the user can move or slide the vibration source 226 onto the outer surface of the outer shaft 110 in conjunction with movement of the air within the balloon catheter 100. Direct contact between the outer surface of the balloon catheter 100 and the vibration source 226 is preferably maintained while the vibration source 226 is moved.

In a step 346, after no new air or bubbles are seen entering into the inflator 224, the vacuum is removed from the inflation lumen 120 of the balloon catheter 100 by slowly releasing the plunger of the inflator 224 to a neutral position. Vibration via the vibration source 226 may continue to be applied during this step, or may be removed.

In a step 348, the stopcock 222 is closed to the balloon catheter 100. When the stopcock 222 is closed to the balloon catheter 100, the inflator 224 and the inflation lumen 120 of the balloon catheter 100 are no longer in fluid communication. The inflation lumen 120 of the balloon catheter 100 remains sealed with respect to atmosphere. At this step of the method, it is no longer required to apply vibration to the balloon catheter 100 via the vibration source 226.

In a step 350, after the stopcock 222 is closed to the balloon catheter, the inflator 224 is detached from the stopcock 222 and purged by advancing the plunger to force the air out of the syringe. Any air that has accumulated in the inflator 224 during the step 344 is released or purged from the inflator 224.

In a step 352, an operator decides or determines whether the balloon catheter 100 is sufficiently purged of air. For example, the operator may visually inspect the balloon catheter 100 to determine whether any additional air bubbles are still present within the balloon catheter 100. The operator may also make the decision whether the balloon catheter 100 is sufficient purged of air based on an observation of the rate and size of air or bubbles seen entering into the inflator 224 during the step 344. If the rate of air or bubbles was relatively slow and/or the size of the air or bubbles was relatively small, the operator may determine that the balloon catheter 100 is sufficiently purged of air. If the operator determines that the balloon catheter 100 is sufficiently purged of air, the balloon catheter preparation method is considered to be complete at a step 354. However, if the operator determines that the balloon catheter 100 is not sufficiently purged of air, the inflator 224 would then be reattached to the stopcock 222 and the above-described steps of using the inflator to apply or pull a vacuum on the inflation lumen 120 of the balloon catheter 100 while vibrating the balloon catheter 100 with the vibration source 226 are repeated until the air or bubbles are fully purged from the balloon 108 and the inflation lumen 120. More particularly, the steps 334, 336, 338, 340, 342, 344, 346, 348, and 350 are repeated as necessary until all air is removed from the balloon catheter.

Figure 4:
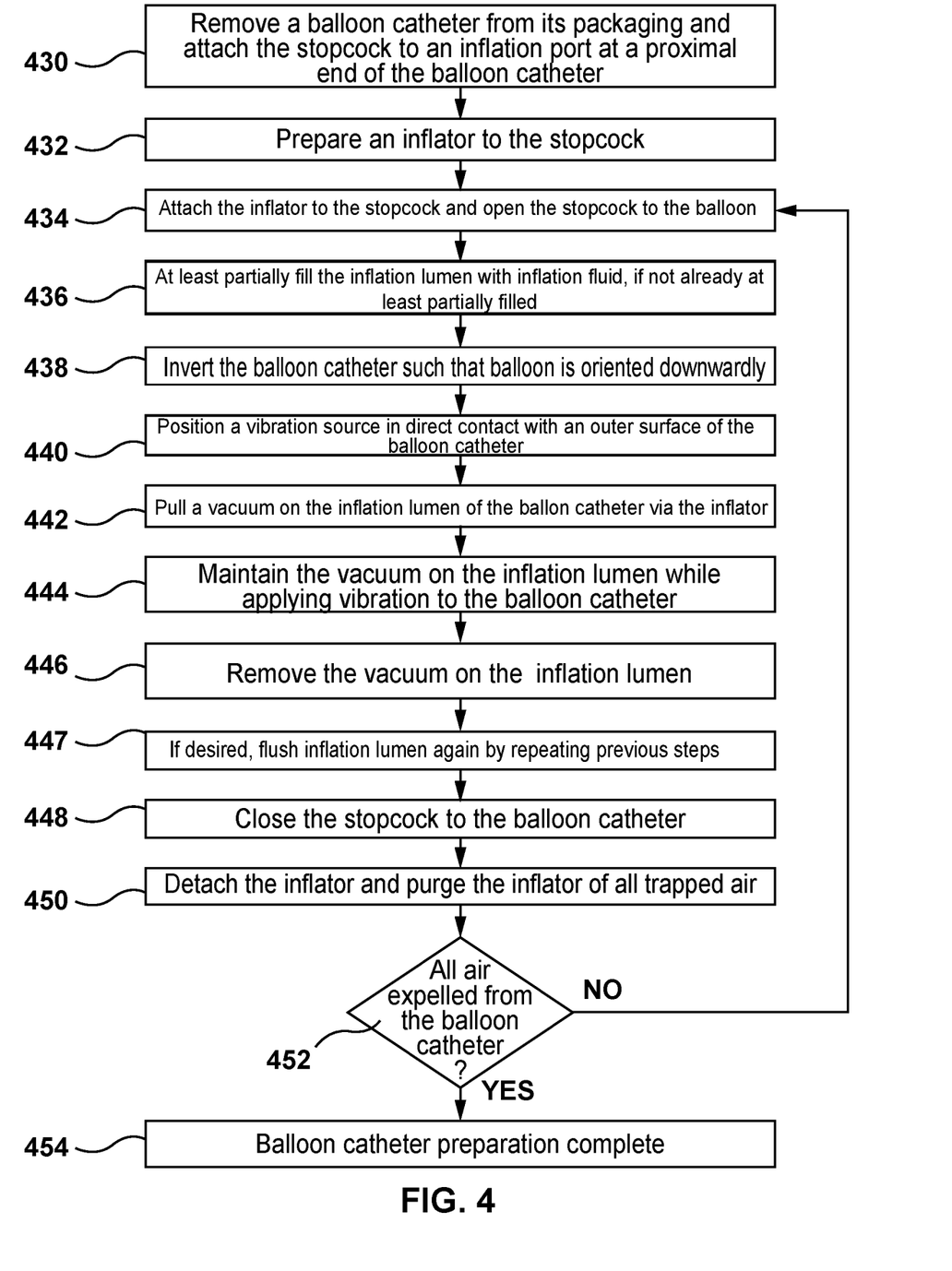
FIG. 4 is a flow chart illustrating a method of purging air from a balloon catheter according to another embodiment hereof.

FIG. 4 illustrates another embodiment hereof in which the inflation lumen 120 may be repeatedly flushed as desired, with vibration being applied while applying vacuum to the balloon catheter, prior to detaching the inflator to purge the inflator of all trapped air. Similar to the method of FIG. 3, the method of FIG. 4 is preferably performed prior to an interventional procedure which utilizes the balloon catheter 100 in situ. This method is particularly advantageous for balloon catheters having larger balloons, such as but not limited to a balloon catheter configured as a delivery device for a replacement heart valve, because the method substantially reduces the length of the catheter preparation time by applying the vibration source 226 to expedite bubble/air removal from the balloon catheter as described above.

In a step 430, similar to the step 330, the balloon catheter 100 is removed from its packaging. The stopcock 222 is attached to the inflation port at the proximal portion 102 of the balloon catheter 100. More particularly, the stopcock 222 is attached to the inflation port of the luer fitting 105 of the hub 104 of the balloon catheter 100. As described above, the distal portion 106 of the balloon catheter 100 includes the balloon 108 and the inflation lumen 120 of the balloon catheter 100 is in fluid communication with the interior of the balloon 108. Although the method of FIG. 4 is described with respect to the balloon catheter 100, it will be understood by those of ordinary skill in the art that this is for sake of illustration only and the methods described herein for purging a balloon catheter of air may be utilized on balloon catheters of any construction and size.

In a step 432, similar to the step 332, the inflator 224 is prepared by at least partially filling the inflator 224 with an inflation fluid. In an embodiment, the inflator 224 is a syringe and the inflation fluid is a radiopaque contrast fluid, or a radiopaque contrast fluid mixed with saline or water. Other suitable biocompatible inflation fluids may be utilized.

In a step 434, similar to the step 334, the inflator 224 is attached to the stopcock 222 which was previously attached to the inflation port of the luer fitting 105 of the hub 104 of the balloon catheter 100 as described above and the stopcock 222 is opened to the balloon catheter 100. When the stopcock 222 is opened to the balloon catheter 100, the inflator 224 and the inflation lumen 120 of the balloon catheter 100 are in fluid communication and the inflation lumen 120 of the balloon catheter 100 is sealed with respect to atmosphere. Alternatively, the inflator 224 may be attached to the stopcock 222 and then the assembly of the inflator 224 and the stopcock 222 may be simultaneously attached to the inflation port at the proximal portion 102 of the balloon catheter 100.

In a step 436, similar to the step 336, the inflation lumen 120 is at least partially filled with the inflation fluid from the inflator 224. In order to at least partially fill the inflation lumen 120 with the inflation fluid from the inflator, the inflation fluid may be injected or inserted into the balloon 108 and the inflation lumen 120 of the balloon catheter 100 via the inflator 224 by advancing the plunger of the inflator 224. In another embodiment, in order to at least partially fill the inflation lumen 120 with the inflation fluid from the inflator, a vacuum may be applied or pulled on the inflation lumen 120 of the balloon catheter 100 via the inflator 224 and then the vacuum may be removed by slowly releasing the plunger of the inflator 224 to a neutral position, thereby at least partially filling the inflation lumen 120 with the inflation fluid from the inflator. More particularly, a user can manually apply or pull a vacuum on the inflation lumen 120 of the balloon catheter 100 by "pulling negative" or retracting the plunger of the inflator 224. When the plunger of the inflator 224 is released to a neutral position, the inflation fluid within the inflator 224 is drawn into the balloon catheter 100 and the inflation lumen 120 at least partially fills with the inflation fluid. Stated another way, removing the vacuum results in inflation fluid from the inflator 224 being pulled into the balloon catheter 100 such that the inflation lumen 120 and the balloon 108 are filled with the inflation fluid. The inflation fluid is drawn into the inflation lumen 120 and balloon 108 as a result of the pressure changes of the enclosed system.

In a step 438 similar to the step 338, the balloon catheter 100 is inverted or positioned in an inverted orientation such that the distal portion 106 including the balloon 108 is oriented below or downwardly relative to the proximal portion 102 of the balloon catheter and the inflator 224 coupled thereto. In an embodiment, the balloon catheter 100 is positioned in a vertical orientation with its distal end including the balloon 108 disposed vertically below the hub 104 and the inflator 224. However, the balloon catheter 100 is not required to be oriented vertically; the balloon catheter 100 may be oriented at an angle so long as the distal portion 106 thereof including the balloon 108 is oriented below or downwardly relative to the inflator 224. As will be described in more detail herein, the positioning of the inflator 224 above the balloon catheter 100 allows air bubbles to ascend or rise through the column of inflation fluid in the inflation lumen 120 and exit from the balloon catheter 100 via the inflator 224.

In a step 440, similar to the step 340, the vibration source 226 is positioned in direct contact with an outer surface of the balloon catheter. In an embodiment, the vibration source 226 is a handheld tool that is configured to be held by a user. In an embodiment, the vibration source 226 includes an outer surface configured to be held by a user and includes an inner surface (not shown) that is configured to make direct physical contact with the outer surface of the balloon 108 and/or the outer surface of the outer shaft 110. For example, the inner surface of the vibration source 226 may have a shape corresponding to the outer surface of the balloon 108 and/or the outer surface of the outer shaft 110.

In a step 442, similar to the step 342, a vacuum is applied or pulled on the inflation lumen 120 of the balloon catheter 100 via the inflator 224. More particularly, a user can manually apply or pull a vacuum on the inflation lumen 120 of the balloon catheter 100 by "pulling negative" or retracting the plunger of the inflator 224. Application of a vacuum results in the evacuation of air from the inflation lumen 120 of the balloon catheter 100. Stated another way, any residual air or gas is purged from the inflation lumen 120 of the balloon catheter 100 and the pressure within the inflation lumen 120 of the balloon catheter 100 is lowered to a pressure lower than atmospheric pressure. In an embodiment, any residual air or gas is purged from the inflation lumen 120 of the balloon catheter 100 until the pressure in the inflation lumen 120 is between 1 PSIA and 12 PSIA. During the step 442, the stopcock 222 remains in its previous position ("open to the balloon catheter 100") and thereby seals the balloon catheter 100 while the inflator 224 pulls a vacuum on the inflation lumen 120 of the balloon catheter 100.

In a step 444, similar to the step 344, the vacuum is maintained on the inflation lumen 120 of the balloon catheter 100 via the inflator 224 while simultaneously applying vibration to the balloon catheter 100 via the vibration source 226. The balloon catheter 100 is vibrated via the vibration source 226 while applying the vacuum on the inflation lumen 120 of the balloon catheter 100 to cause air within the balloon 108 of the balloon catheter 100 or air within the inflation lumen 120 of the balloon catheter 100 to move upwards through the column of inflation fluid towards the proximal end of the balloon catheter 100 and the inflator 224. Stated another way, vibrating the balloon catheter 100 with the vibration source 226 causes any air or bubbles entrapped in the balloon catheter 100 to ascend out of the balloon 108 and inflation lumen 120 until such air or bubbles exit from the balloon catheter 100 and enter into the inflator 224. As air or bubbles exit from the balloon catheter 100 and enter into the inflator 224, the user can visually see such air or bubbles in the inflator 224. The vacuum is maintained on the inflation lumen 120 of the balloon catheter 100 via the inflator 224 while simultaneously applying vibration to the balloon catheter 100 until no new air or bubbles are seen entering into the inflator 224. For example, in an embodiment, the vacuum is maintained on the inflation lumen and vibration is simultaneously applied on the balloon catheter for between 15 and 45 seconds. In an embodiment, the vacuum is maintained on the inflation lumen and vibration is simultaneously applied on the balloon catheter for approximately 30 seconds. Although described herein that vibration is applied during the step 442, vibration may also be applied during previous method steps as well. For example, vibration may begin immediately after the vibration source 226 is placed into direct contact with the balloon catheter 100 or the vibration may begin prior to or at the same time as the step 442 when the vacuum is initially pulled or applied to the inflation lumen 120.

In an embodiment, during the step 444, the vibration source 226 is moved or slid along the outer surface of the balloon catheter 100 while vibrating the balloon catheter. For example, the vibration source 226 may originally be placed in direct physical contact with the outer surface of the balloon 108. As the air or bubbles entrapped in the balloon 108 ascend into the inflation lumen 120, the user can move or slide the vibration source 226 onto the outer surface of the outer shaft 110 in conjunction with movement of the air within the balloon catheter 100. Direct contact between the outer surface of the balloon catheter 100 and the vibration source 226 is preferably maintained while the vibration source 226 is moved.

In a step 446, similar to the step 346, after no new air or bubbles are seen entering into the inflator 224, the vacuum is removed from the inflation lumen 120 of the balloon catheter 100 by slowly releasing the plunger of the inflator 224 to a neutral position. Vibration via the vibration source 226 may continue to be applied during this step, or may be removed.

In a step 447, steps 442, 444, and 446 may be repeated if desired to flush the inflation lumen 120 of the balloon catheter 100 again. More particularly, it may be desired to flush the inflation lumen 120 several times before proceeding to the later method steps of closing and detaching the stopcock 222 and purging the inflator 224 of all trapped air. Thus, an operator may choose to repeat the steps of pulling a vacuum, maintaining the vacuum while simultaneously applying vibration to the balloon catheter 100, and then removing the vacuum as many times as desired before proceeding to the next method steps.

In a step 448, similar to the step 348, the stopcock 222 is closed to the balloon catheter 100. When the stopcock 222 is closed to the balloon catheter 100, the inflator 224 and the inflation lumen 120 of the balloon catheter 100 are no longer in fluid communication. The inflation lumen 120 of the balloon catheter 100 remains sealed with respect to atmosphere. At this step of the method, it is no longer required to apply vibration to the balloon catheter 100 via the vibration source 226.

In a step 450, similar to the step 350, after the stopcock 222 is closed to the balloon catheter, the inflator 224 is detached from the stopcock 222 and purged by advancing the plunger to force the air out of the syringe. Any air that has accumulated in the inflator 224 during the previous steps is released or purged from the inflator 224.

In a step 452, similar to the step 352, an operator decides or determines whether the balloon catheter 100 is sufficiently purged of air. For example, the operator may visually inspect the balloon catheter 100 to determine whether any additional air bubbles are still present within the balloon catheter 100. The operator may also make the decision whether the balloon catheter 100 is sufficient purged of air based on an observation of the rate and size of air or bubbles seen entering into the inflator 224 during the step 444. If the rate of air or bubbles was relatively slow and/or the size of the air or bubbles was relatively small, the operator may determine that the balloon catheter 100 is sufficiently purged of air. If the operator determines that the balloon catheter 100 is sufficiently purged of air, the balloon catheter preparation method is considered to be complete at a step 454. However, if the operator determines that the balloon catheter 100 is not sufficiently purged of air, the inflator 224 would then be reattached to the stopcock 222 and the above-described steps of using the inflator to apply or pull a vacuum on the inflation lumen 120 of the balloon catheter 100 while vibrating the balloon catheter 100 with the vibration source 226 are repeated until the air or bubbles are fully purged from the balloon 108 and the inflation lumen 120. More particularly, the steps 434, 436, 438, 440, 442, 444, 446, 447, 448, and 450 are repeated as necessary until all air is removed from the balloon catheter.

Figure 5:
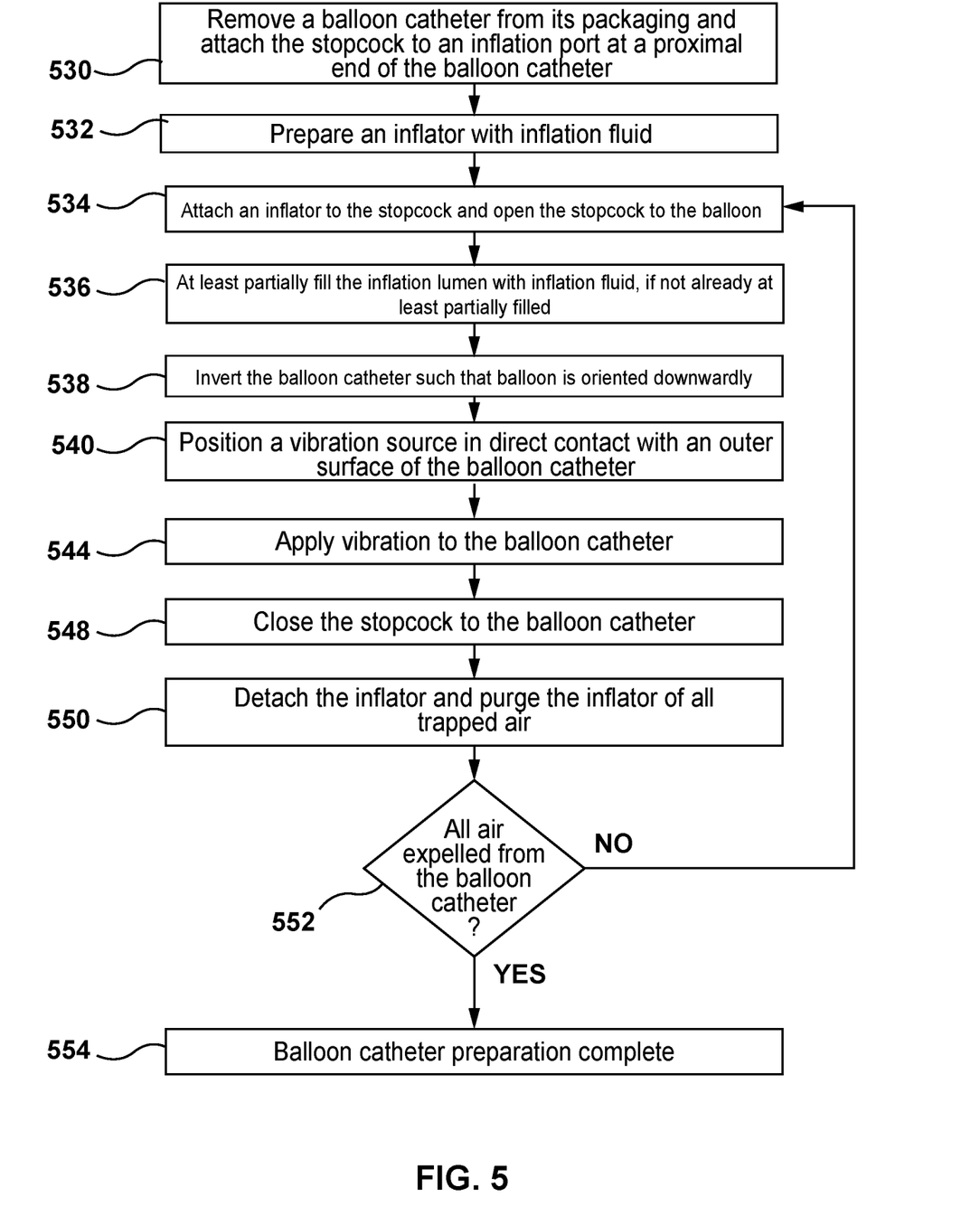
FIG. 5 is a flow chart illustrating a method of purging air from a balloon catheter according to another embodiment hereof.

In the above-described methods of FIGS. 3 and 4, the inflator 224 is used to manually pull vacuum as well as to inject or insert inflation fluid into the balloon catheter 100 during the described methods. However, in another embodiment, pulling a vacuum with the inflator 224 is not required as shown in the method depicted in FIG. 5. Stated another way, in an embodiment, only vibration via the vibration source 226 may be utilized to purge air from the balloon catheter 100. Similar to the method of FIG. 3 the method of FIG. 5 is preferably performed prior to an interventional procedure which utilizes the balloon catheter 100 in situ. This method is particularly advantageous for balloon catheters having larger balloons, such as but not limited to a balloon catheter configured as a delivery device for a replacement heart valve, because the method substantially reduces the length of the catheter preparation time by applying the vibration source 226 to expedite bubble/air removal from the balloon catheter as described above.

In a step 530, similar to the step 330, the balloon catheter 100 is removed from its packaging. The stopcock 222 is attached to the inflation port at the proximal portion 102 of the balloon catheter 100. More particularly, the stopcock 222 is attached to the inflation port of the luer fitting 105 of the hub 104 of the balloon catheter 100. As described above, the distal portion 106 of the balloon catheter 100 includes the balloon 108 and the inflation lumen 120 of the balloon catheter 100 is in fluid communication with the interior of the balloon 108. Although the method of FIG. 5 is described with respect to the balloon catheter 100, it will be understood by those of ordinary skill in the art that this is for sake of illustration only and the methods described herein for purging a balloon catheter of air may be utilized on balloon catheters of any construction and size.

In a step 532 similar to the step 332, the inflator 224 is prepared by at least partially filling the inflator 224 with an inflation fluid. In an embodiment, the inflator 224 is a syringe and the inflation fluid is a radiopaque contrast fluid, or a radiopaque contrast fluid mixed with saline or water. Other suitable biocompatible inflation fluids may be utilized.

In a step 534, similar to the step 334, the inflator 224 is attached to the stopcock 222 which was previously attached to the inflation port of the luer fitting 105 of the hub 104 of the balloon catheter 100 as described above and the stopcock 222 is opened to the balloon catheter 100. When the stopcock 222 is opened to the balloon catheter 100, the inflator 224 and the inflation lumen 120 of the balloon catheter 100 are in fluid communication and the inflation lumen 120 of the balloon catheter 100 is sealed with respect to atmosphere. Alternatively, the inflator 224 may be attached to the stopcock 222 and then the assembly of the inflator 224 and the stopcock 222 may be simultaneously attached to the inflation port at the proximal portion 102 of the balloon catheter 100.

In a step 536, similar to the step 336, the inflation lumen 120 is at least partially filled with the inflation fluid from the inflator 224. In order to at least partially fill the inflation lumen 120 with the inflation fluid from the inflator, the inflation fluid may be injected or inserted into the balloon 108 and the inflation lumen 120 of the balloon catheter 100 via the inflator 224 by advancing the plunger of the inflator 224. In another embodiment, in order to at least partially fill the inflation lumen 120 with the inflation fluid from the inflator, a vacuum may be applied or pulled on the inflation lumen 120 of the balloon catheter 100 via the inflator 224 and then the vacuum may be removed by slowly releasing the plunger of the inflator 224 to a neutral position, thereby at least partially filling the inflation lumen 120 with the inflation fluid from the inflator. More particularly, a user can manually apply or pull a vacuum on the inflation lumen 120 of the balloon catheter 100 by "pulling negative" or retracting the plunger of the inflator 224. When the plunger of the inflator 224 is released to a neutral position, the inflation fluid within the inflator 224 is drawn into the balloon catheter 100 and the inflation lumen 120 at least partially fills with the inflation fluid. Stated another way, removing the vacuum results in inflation fluid from the inflator 224 being pulled into the balloon catheter 100 such that the inflation lumen 120 and the balloon 108 are filled with the inflation fluid. The inflation fluid is drawn into the inflation lumen 120 and balloon 108 as a result of the pressure changes of the enclosed system.

In a step 538, similar to the step 338, the balloon catheter 100 is inverted or positioned in an inverted orientation such that the distal portion 106 including the balloon 108 is oriented below or downwardly relative to the proximal portion 102 of the balloon catheter and the inflator 224 coupled thereto. In an embodiment, the balloon catheter 100 is positioned in a vertical orientation with its distal end including the balloon 108 disposed vertically below the hub 104 and the inflator 224. However, the balloon catheter 100 is not required to be oriented vertically; the balloon catheter 100 may be oriented at an angle so long as the distal portion 106 thereof including the balloon 108 is oriented below or downwardly relative to the inflator 224. As will be described in more detail herein, the positioning of the inflator 224 above the balloon catheter 100 allows air bubbles to ascend or rise through the column of inflation fluid in the inflation lumen 120 and exit from the balloon catheter 100 via the inflator 224.

In a step 540, similar to the step 340, the vibration source 226 is positioned in direct contact with an outer surface of the balloon catheter. In an embodiment, the vibration source 226 is a handheld tool that is configured to be held by a user. In an embodiment, the vibration source 226 includes an outer surface configured to be held by a user and includes an inner surface (not shown) that is configured to make direct physical contact with the outer surface of the balloon 108 and/or the outer surface of the outer shaft 110. For example, the inner surface of the vibration source 226 may have a shape corresponding to the outer surface of the balloon 108 and/or the outer surface of the outer shaft 110.

In a step 544, vibration is applied to the balloon catheter 100 via the vibration source 226. The balloon catheter 100 is vibrated via the vibration source 226 to cause air within the balloon 108 of the balloon catheter 100 or air within the inflation lumen 120 of the balloon catheter 100 to move upwards towards the proximal end of the balloon catheter 100 and the inflator 224. Stated another way, vibrating the balloon catheter 100 with the vibration source 226 causes any air or bubbles entrapped in the balloon catheter 100 to ascend out of the balloon 108 and inflation lumen 120 until such air or bubbles exit from the balloon catheter 100 and enter into the inflator 224. As air or bubbles exit from the balloon catheter 100 and enter into the inflator 224, the user can visually see such air or bubbles in the inflator 224. Vibration is applied to the balloon catheter 100 until no new air or bubbles are seen entering into the inflator 224. For example, in an embodiment, vibration is applied on the balloon catheter for between 15 and 45 seconds. In an embodiment, vibration is applied on the balloon catheter for approximately 30 seconds.

In an embodiment, during the step 544, the vibration source 226 is moved or slid along the outer surface of the balloon catheter 100 while vibrating the balloon catheter. For example, the vibration source 226 may originally be placed in direct physical contact with the outer surface of the balloon 108. As the air or bubbles entrapped in the balloon 108 ascend into the inflation lumen 120, the user can move or slide the vibration source 226 onto the outer surface of the outer shaft 110 in conjunction with movement of the air within the balloon catheter 100. Direct contact between the outer surface of the balloon catheter 100 and the vibration source 226 is preferably maintained while the vibration source 226 is moved.

In a step 548, similar to the step 348, the stopcock 222 is closed to the balloon catheter 100. When the stopcock 222 is closed to the balloon catheter 100, the inflator 224 and the inflation lumen 120 of the balloon catheter 100 are no longer in fluid communication. The inflation lumen 120 of the balloon catheter 100 remains sealed with respect to atmosphere. At this step of the method, it is no longer required to apply vibration to the balloon catheter 100 via the vibration source 226.

In a step 550, similar to the step 350, after the stopcock 222 is closed to the balloon catheter, the inflator 224 is detached from the stopcock 222 and purged by advancing the plunger to force the air out of the syringe. Any air that has accumulated in the inflator 224 during the step 544 is released or purged from the inflator 224.

In a step 552, similar to the step 352, an operator decides or determines whether the balloon catheter 100 is sufficiently purged of air. For example, the operator may visually inspect the balloon catheter 100 to determine whether any additional air bubbles are still present within the balloon catheter 100. The operator may also make the decision whether the balloon catheter 100 is sufficient purged of air based on an observation of the rate and size of air or bubbles seen entering into the inflator 224 during the step 544. If the rate of air or bubbles was relatively slow and/or the size of the air or bubbles was relatively small, the operator may determine that the balloon catheter 100 is sufficiently purged of air. If the operator determines that the balloon catheter 100 is sufficiently purged of air, the balloon catheter preparation method is considered to be complete at a step 554. However, if the operator determines that the balloon catheter 100 is not sufficiently purged of air, the inflator 224 would then be reattached to the stopcock 222 and the above-described steps including vibrating the balloon catheter 100 with the vibration source 226 are repeated until the air or bubbles are fully purged from the balloon 108 and the inflation lumen 120. More particularly, the steps 534, 536, 538, 540, 544, 548, and 550 are repeated as necessary until all air is removed from the balloon catheter.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

The invention claimed is:

1. A method for purging a balloon catheter of air, the method comprising the steps of:
    inserting an inflation fluid into a balloon and an inflation lumen of the balloon catheter, wherein the inflation lumen is in fluid communication with the balloon;
    positioning the balloon catheter in an inverted orientation with a distal end thereof disposed below a proximal end thereof, wherein the distal end of the balloon catheter includes the balloon;
    positioning a vibration source in direct contact with an outer surface of the balloon of the balloon catheter and/or an outer surface of an outer shaft of the balloon catheter;
    vibrating the balloon catheter with the vibration source to cause air within the balloon of the balloon catheter or air within the inflation lumen of the balloon catheter to move upwards towards the proximal end of the balloon catheter; and
    moving the vibration source along the outer surface of the balloon catheter while vibrating the balloon catheter, wherein the direct contact between the outer surface of the balloon catheter and the vibration source is maintained during the step of moving the vibration source.

2. The method of claim 1, wherein the method for purging the balloon catheter of air is performed prior to an interventional procedure.

3. The method of claim 1, further comprising the steps of:
    attaching an inflator to the proximal end of the balloon catheter; and
    using the inflator to apply a vacuum on the inflation lumen of the balloon catheter while vibrating the balloon catheter with the vibration source.

4. The method of claim 3, wherein the inflator is a syringe having the inflation fluid therein.

5. The method of claim 3, further comprising the steps of:
    detaching the inflator from the proximal end of the balloon catheter after the step of using the inflator to apply the vacuum on the inflation lumen of the balloon catheter; and
    removing air that has accumulated in the inflator from the inflator.

6. The method of claim 5, further comprising the steps of:
    reattaching the inflator to the proximal end of the balloon catheter after the step of removing air that from the inflator; and
    repeating the step of using the inflator to apply the vacuum on the inflation lumen of the balloon catheter while vibrating the balloon catheter with the vibration source.

7. The method of claim 3, wherein a stopcock seals the balloon catheter during the step of using the inflator to apply the vacuum on the inflation lumen of the balloon catheter.

8. The method of claim 1, wherein the balloon catheter is configured as a delivery device for a replacement aortic heart valve.

9. A method for purging a balloon catheter of air, the method comprising the steps of:
    inserting an inflation fluid into a balloon and an inflation lumen of a balloon catheter, wherein the inflation lumen is in fluid communication with the balloon;
    positioning the balloon catheter in an inverted orientation with a distal end thereof disposed below a proximal end thereof, wherein the distal end of the balloon catheter includes the balloon;
    positioning a vibration source in direct contact with an outer surface of the balloon of the balloon catheter and/or an outer surface of an outer shaft of the balloon catheter;
    applying a vacuum on the inflation lumen of the balloon catheter;
    vibrating the balloon catheter with the vibration source while applying the vacuum on the inflation lumen of the balloon catheter to cause any air within the balloon of the balloon catheter and any air within the inflation lumen of the balloon catheter to move upwards through the inflation fluid towards the proximal end of the balloon catheter; and
    moving the vibration source along the outer surface of the balloon catheter while vibrating the balloon catheter, wherein the direct contact between the outer surface of the balloon catheter and the vibration source is maintained during the step of moving the vibration source.

10. The method of claim 9, wherein the method for purging the balloon catheter of air is performed prior to an interventional procedure.

11. The method of claim 9, wherein the steps of inserting the inflation fluid into the balloon and the inflation lumen and applying the vacuum on the inflation lumen are performed via an inflator attached to the proximal end of the balloon catheter.

12. The method of claim 11, wherein the inflator is a syringe.

13. The method of claim 11, further comprising the steps of:
    detaching the inflator from the proximal end of the balloon catheter after the step of vibrating the balloon catheter with the vibration source while applying the vacuum on the inflation lumen of the balloon catheter; and
    removing any air that has accumulated in the inflator from the inflator.

14. The method of claim 13, further comprising the steps of:
    reattaching the inflator to the proximal end of the balloon catheter after the step of removing any air that has accumulated in the inflator from the inflator; and
    repeating the method for purging the balloon catheter of air until all air is purged from the balloon catheter.

15. The method of claim 9, wherein a stopcock seals the balloon catheter during the step of applying the vacuum on the inflation lumen of the balloon catheter.

16. The method of claim 9, wherein the balloon catheter is configured as a delivery device for a replacement aortic heart valve.

17. A method for purging a balloon catheter of air, the method comprising the steps of:
  inserting an inflation fluid into a balloon and an inflation lumen of a balloon catheter, wherein the inflation lumen is in fluid communication with the balloon;
  positioning the balloon catheter in an inverted orientation with a distal end thereof disposed below a proximal end thereof, wherein the distal end of the balloon catheter includes the balloon;
  positioning a vibration source in direct contact with an outer surface of the balloon of the balloon catheter and/or an outer surface of an outer shaft of the balloon catheter;
  vibrating the balloon catheter with the vibration source;
  applying a vacuum on the inflation lumen of the balloon catheter; and
  moving the vibration source along the outer surface of the balloon catheter while vibrating the balloon catheter, wherein the direct contact between the outer surface of the balloon catheter and the vibration source is maintained during the step of moving the vibration source;
  wherein the steps of vibrating the balloon catheter and applying the vacuum are performed simultaneously and are performed prior to an interventional procedure which utilizes the balloon catheter in situ.

18. The method of claim 17, wherein the balloon catheter is configured as a delivery device for a replacement aortic heart valve.

* * * * *